United States Patent
Duan

(10) Patent No.: US 10,314,514 B2
(45) Date of Patent: Jun. 11, 2019

(54) SYSTEM AND METHOD FOR USING A CAPSULE DEVICE

(71) Applicant: Ankon Medical Technologies (Shanghai), LTD., Shanghai (CN)

(72) Inventor: Xiaodong Duan, Pleasanton, CA (US)

(73) Assignee: ANKON MEDICAL TECHNOLOGIES (SHANGHAI) CO., LTD., Shanghai (CN)

( * ) Notice: Subject to any disclaimer, the term of this patent is extended or adjusted under 35 U.S.C. 154(b) by 210 days.

(21) Appl. No.: 15/168,065

(22) Filed: May 29, 2016

(65) Prior Publication Data
US 2017/0340242 A1    Nov. 30, 2017

(51) Int. Cl.
| | | |
|---|---|---|
| *A61B 1/00* | (2006.01) | |
| *A61B 5/06* | (2006.01) | |
| *A61B 1/04* | (2006.01) | |
| *A61B 1/06* | (2006.01) | |
| *A61B 5/00* | (2006.01) | |
| *A61B 5/07* | (2006.01) | |

(52) U.S. Cl.
CPC .......... *A61B 5/067* (2013.01); *A61B 1/00006* (2013.01); *A61B 1/00016* (2013.01); *A61B 1/041* (2013.01); *A61B 1/0684* (2013.01); *A61B 5/073* (2013.01); *A61B 5/7475* (2013.01); *A61B 5/4255* (2013.01); *A61B 5/6861* (2013.01); *A61B 2562/0219* (2013.01)

(58) Field of Classification Search
CPC ............ A61B 1/00025; A61B 1/00036; A61B 1/00006; A61B 1/00016; A61B 1/041; A61B 5/067; A61B 5/073; A61B 2560/0209

USPC ................................................... 600/118, 117
See application file for complete search history.

(56) References Cited

U.S. PATENT DOCUMENTS

| | | | | |
|---|---|---|---|---|
| 2002/0032366 A1* | 3/2002 | Iddan | ................ | A61B 1/00036 600/117 |
| 2004/0204630 A1* | 10/2004 | Gilad | .................... | A61B 1/041 600/160 |
| 2004/0253304 A1* | 12/2004 | Gross | .................... | A61B 1/041 424/451 |
| 2005/0049488 A1* | 3/2005 | Homan | ............. | A61B 1/00036 600/431 |
| 2005/0054897 A1* | 3/2005 | Hashimoto | ........... | A61B 1/041 600/118 |
| 2005/0065441 A1* | 3/2005 | Glukhovsky | .......... | A61B 1/041 600/476 |
| 2005/0192476 A1* | 9/2005 | Homan | ............. | A61B 1/00006 600/118 |
| 2007/0098379 A1* | 5/2007 | Wang | ................ | A61B 1/00009 396/14 |
| 2007/0165932 A1* | 7/2007 | Nishimura | ......... | A61B 1/00016 382/128 |
| 2007/0191677 A1* | 8/2007 | Nishimura | ......... | A61B 1/00009 600/109 |

(Continued)

*Primary Examiner* — Timothy J Neal
*Assistant Examiner* — Jae Woo
(74) *Attorney, Agent, or Firm* — Treasure IP Group, LLC

(57) ABSTRACT

A capsule device configured to navigate through a patient's GI track is disclosed. System and method to turn on the capsule device based on acceleration is described. First the capsule is monitored at a slow sampling mode. Then the capsule is monitored at a fast sampling mode. A user can input hand motion to change the acceleration to turn on the capsule device.

12 Claims, 3 Drawing Sheets

(56) References Cited

U.S. PATENT DOCUMENTS

| | | | |
|---|---|---|---|
| 2007/0292011 A1* | 12/2007 | Nishimura | A61B 1/00009 382/128 |
| 2008/0170846 A1* | 7/2008 | Wang | A61B 1/00096 396/182 |
| 2008/0242926 A1* | 10/2008 | Nishino | A61B 1/04 600/109 |
| 2009/0196476 A1* | 8/2009 | Inoue | A61B 1/04 382/128 |
| 2009/0274347 A1* | 11/2009 | Gat | A61B 1/00036 382/128 |
| 2009/0322865 A1* | 12/2009 | Wang | A61B 1/00009 348/68 |
| 2010/0220179 A1* | 9/2010 | Wang | A61B 1/00009 348/68 |
| 2011/0054255 A1* | 3/2011 | Schmidt | A61B 1/00158 600/118 |
| 2011/0210621 A1* | 9/2011 | Iwaisako | A61B 1/00029 307/104 |
| 2013/0261410 A1* | 10/2013 | Davenport | A61B 5/073 600/302 |
| 2014/0155709 A1* | 6/2014 | Ikai | A61B 1/00006 600/302 |
| 2016/0213235 A1* | 7/2016 | Hasegawa | A61B 1/045 |
| 2017/0127922 A1* | 5/2017 | Godo | A61B 1/00045 |
| 2017/0231470 A1* | 8/2017 | Yanagidate | A61B 1/00 600/118 |
| 2017/0280977 A1* | 10/2017 | Ikai | A61B 1/00158 |

\* cited by examiner

SYSTEM AND METHOD FOR USING A CAPSULE DEVICE

CROSS-REFERENCE

None.

TECHNICAL FIELD OF THE DISCLOSURE

This patent application relates to the art of capsule devices to be used in medical related applications, and more particularly, to the art of systems and methods to turn on a capsule device from shelf state to a working state.

BACKGROUND OF THE DISCLOSURE

Capsule endoscopy not only has been demonstrated to be very successful in examining patient's interior, but shows clear advantage over traditional endoscope techniques when it comes to examining a patient's small intestine, where areas or portions of the gastrointestinal tract are not readily accessible by traditional standard endoscopy techniques.

Vibration capsule by acting on human colonic wall can alleviate colon spasm and promote colonic motility, treat constipation, and promote beauty and health. Further, vibration capsules have shown to promote the small intestine peristalsis, reduce the absorption of food in the small intestine, and achieve weight loss effects.

However, for both endoscope type of capsule and vibration type capsule, maintaining low power consumption and reducing unnecessary power usage during shelf or storage time remains a challenge. The power consumption of the capsule device is proportional to the duration of working period. It is commonly accepted that saving most of the power for working period and effectively separating working period and non-working period is very practical and important.

In another words, there is a need to precisely turn on the capsule when it is really needed and otherwise keeping the capsule at a low power consumption at shelf or storage period.

SUMMARY OF THE INVENTION

The present invention discloses a system and method to turn on a capsule device.

It is one object of the present invention to provide a capsule device has long shelf time by having low power consumption during shelf time, for example to keep the shelf time for at least a year.

It is another object of the present invention to provide a method to accurate turn on the capsule without falsely turning it on.

It is still another object of the present invention that the method to turn on the capsule must require the least possible power as well as the turn on protocol must be easy to adopt for an average consumer.

It is yet another object of the present invention to provide method to turn on the capsule or the turn-on protocol does not require an additional part that adds to either weight or cost of the capsule manufacture.

The method to turn on the capsule device disclosed herein is directed to change a capsule from a non-working state to a working state based on the acceleration data detected by an acceleration sensor placed in situ. The method steps comprises monitoring an acceleration of the capsule in three dimensions at a low sampling frequency when the capsule is known to be in a non-working state; when a collected acceleration data is above a first threshold value, changing the measurement sampling frequency to a high sampling frequency and continuing to monitor the acceleration of the capsule in three dimensions; when the collected acceleration data at the high sampling frequency continues to be above a second threshold value, preparing the capsule to pre-working state by requesting confirmation from a user of the capsule. In the present method, the low sampling frequency is preferably to between 2-10 Hz and the high sampling frequency is preferably to be between 20-1000 Hz. The time duration for the high sampling frequency detection is no more than 3 seconds and the time duration for the pre-working state is no more than 10 seconds.

The system, disclosed herein to be used in conjunction with the above method, comprises an acceleration sensor, detecting an acceleration of the capsule in three dimensions at two or more different frequencies; a microcontroller unit, configured to take input from the acceleration sensor, perform calculations and compare with a first and second threshold values; capsule initiation unit, to request confirmation for a user and a power supply providing power to the acceleration sensor, microcontroller unit and capsule initiation unit. The acceleration sensor in the present invention is an accelerometer (g-sensor).

In one aspect of the present invention, in one example, the capsule initiation unit further comprises a wireless communication unit.

In a second aspect of the present invention, in one example, the method further comprises a step of instructing to turn on the capsule through a wireless communication unit.

In a second aspect of the present invention, in another example, the method further comprises a step of requesting a confirmation from a user by turning on a LED inside of the capsule.

In a second aspect of the present invention, in another example, the method further comprises a step of requesting a confirmation from a user suggesting and detecting a hand motion of a user while having the capsule in hand.

BRIEF DESCRIPTION OF THE DRAWINGS

Exemplary embodiments of the disclosure will be more clearly understood from the following detailed description taken in conjunction with the accompanying drawings in which.

DETAILED DESCRIPTION OF SELECTED EXAMPLES

Figure 1:
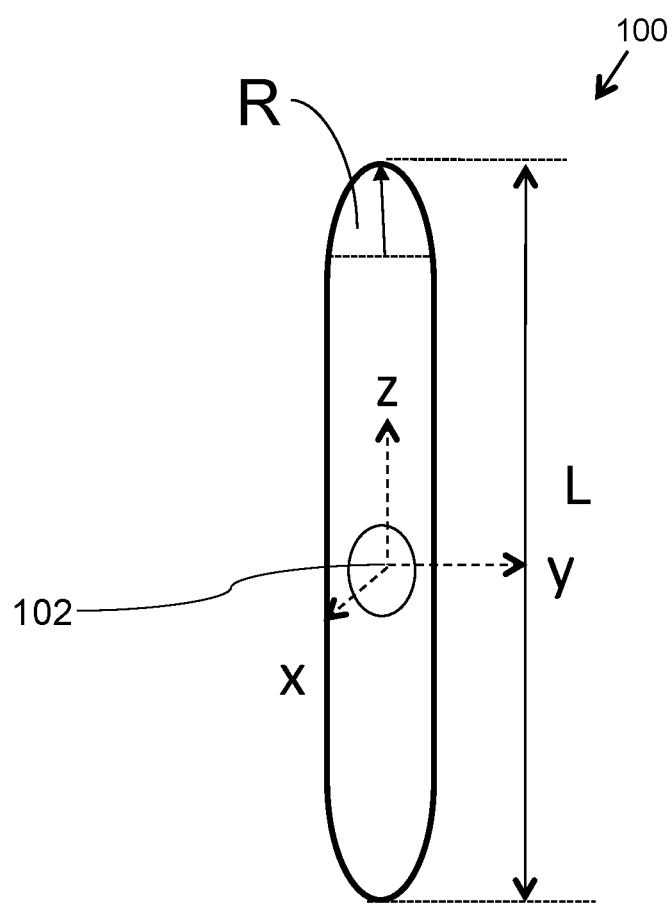
FIG. 1 depicts a schematic diagram of an exemplary capsule device in accordance with aspects of the present invention.

Hereinafter, selected examples of a system for a capsule device to be placed in a target location and methods of using the same will be described in detail with reference to the accompanying drawings. For simplicity purpose, the capsule device is explained in the context of biomedical applications, i.e. the target location is an in vivo location, for example a location inside a digestive tract. For simplicity purpose, the medical device disclosed herein is designed to be placed in vivo. One of the non-invasive methods of delivery is by swallow into a digestive tract. Therefore the medical device disclose herein is referred as a capsule, which should not be construed as a limitation for its shape, dimension or size. The capsule device disclosed herein and methods of using the same can be implemented for many other applications as long as there is a in situ movement generation means, a control module that can mange the movement generation means and a wireless communication module to communicate with the control module.

In the scope of the present invention, fast sampling mode means collect measurement data under high sampling frequency. Slow sampling mode means collect measurement data under low sampling frequency. Acceleration data along one axis is the detected acceleration data along that particular axis. Combined acceleration value or combined acceleration data, or total acceleration data is the calculated root square of two or more single acceleration value along one individual axis. For example total acceleration of a capsule when individual acceleration value along axis a (Aa) and axis b (Ab) is sqrt(ax^2+ay^2+az^2). In the scope of the present invention, when a sensor data is recited, it can be either an individual acceleration data along one axis, or a combined acceleration data that is the calculated after the individual acceleration data along two or more axes have been measured.

It will be appreciated by those skilled in the art that the following discussion is for demonstration purposes, and should not be interpreted as a limitation. Other variances within the scope of this disclosure are also applicable.

The structure and method of using a capsule device is described in detail below. Elements in the drawings are
   100 capsule device
   102 acceleration sensor A capsule system comprises a capsule device, configured to be placed in inside a patient's GI track. In one embodiment, the capsule communicate with an external operation system is placed outside of a patient's body. In one example, the external device is portable device such as a smart phone. A basic capsule device, is configured to communicate with the external operation system through a wireless communication network.

The present invention is directed to systems and methods how a capsule can be effectively changed from a non-working state to a working state. In present invention, a sensor is employed to place inside the capsule device, and the sensor is connected to a microcontroller unit, which configured to take input from the acceleration sensor. Based on the measured changes detected by the sensor, the microcontroller "guesses" if the capsule intends to be in a working state or non-working state by sending out instructions to take more measurement at different conditions and/or request a confirm from a user to input commands either through a user interface or not through a user interface.

In accordance with the aspects of the present invention, in one embodiment, the sensor enclosed in the capsule is a motion sensor. First the motion sensor is calibrated with a normal shelf motion value. In one example, the motion sensor measures a motion data, the sensor data is compared with the shelf motion value and then decide if more measurement is needed or a user confirmation should be requested.

As the goal of the present invention, is to maintain low power consumption and reduce unnecessary power usage during shelf or storage time and effectively and accurately change to working period from non-working period when that is confirmed by a user.

In a preferred embodiment of the present invention, the sensor enclosed in the capsule is an acceleration sensor. In one example, first the acceleration sensor is calibrated with a normal shelf acceleration value. In one example, the acceleration sensor measures an acceleration data, the sensor data is compared with the shelf acceleration value and then decide if more measurement is needed or a user confirmation should be sent.

When the sensor is an acceleration sensor, in another example, based on the acceleration data detected by an acceleration sensor placed inside the capsule and its comparison with a first threshold acceleration value, the microcontroller inside the capsule will decide if more measurement is needed or a user confirmation should be requested.

The present invention discloses a method to change capsule from a non-working state to a working state, or in short turning on the capsule. The method steps comprise first monitoring an acceleration of the capsule in three dimensions at a first sampling frequency when the capsule is known to be in a non-working state. When a collected acceleration data is determined to be equal to or greater than a first threshold acceleration value, then more measurement under a different condition is performed. In one example, the step of performing more measurement under different condition include changing the measurement sampling frequency to a second sampling frequency and continuing to monitor the acceleration of the capsule in three dimensions; when the collected acceleration data at the second sampling frequency continues to be above a second threshold acceleration value, then placing the capsule in a pre-working state. The step of placing the capsule in pre-working state including requesting confirmation from a user of the capsule. In the present invention, the second sampling frequency is higher than the first sampling frequency so that the acceleration data is more evident to detect to avoid false positive or false negative information.

In the present method, in one example, the first sampling frequency is between 0.2-10 Hz In another example, the first sampling frequency is between 0.2-8 Hz. In another example, the first sampling frequency is between 0.2-6 Hz. In another example, the first sampling frequency is between 0.2-5 Hz. In another example, the first sampling frequency is between 0.2-4 Hz. In another example, the first sampling frequency is between 0.2-3 Hz. In another example, the first sampling frequency is between 0.2-2 Hz. In another example, the first sampling frequency is between 0.2-1 Hz.

In the present method, in one example, the second sampling frequency is between 10-2000 Hz. In another example, the second sampling frequency is between 10-1000 Hz. In another example, the second sampling frequency is between 10-500 Hz. In another example, the second sampling frequency is between 10-250 Hz. In another example, the second sampling frequency is between 10-120 Hz. In another example, the second sampling frequency is between 10-60 Hz. In another example, the second sampling frequency is between 10-40 Hz. In another example, the second sampling frequency is between 10-20 Hz.

The time period when capsule is monitored under the first sampling frequency is defined as a first acceleration period. At the first acceleration period, the capsule under non-working state, which includes a shelf time period, storage period or a rest period in between working period.

The time period when capsule is monitored under the second sampling frequency is defined as a second acceleration period. At the second acceleration period, the capsule is continued to be monitored for acceleration data and the acceleration data is collected and compared with the second threshold acceleration value. However the second acceleration period differs the first acceleration period in that the second acceleration period has a time limitation. The time limitation is driven by the low power consumption requirement. In one example, the second acceleration period is less than 5 seconds. In another example, the second acceleration period is less than 4 seconds. In another example, the second acceleration period is less than 3 seconds. In another example, the second acceleration period is less than 2 seconds.

The time period that the capsule placed under pre-working state is defined as a third acceleration period. In general, the third acceleration period last less than 10 seconds.

At the third acceleration period, in one example, while the capsule is conditioned at pre-working state, the capsule is continued to be monitored for acceleration data and the acceleration data is continued to be collected and compared with a third or fourth threshold acceleration value. In one instance, the combined total acceleration value on both a and b axes are calculated after they are collected and compared with a third threshold acceleration value. In another instance, the acceleration value on individual axis are measured, collected and compared with a fourth threshold acceleration value. In still another instance, the combined total acceleration value on more than one axes, for example, both a and b axes, are calculated after they are collected and compared with a third threshold acceleration value, and if the combined acceleration value is greater or equal to the third threshold acceleration value, then individual acceleration data along two more individual axis is measured and compared with a fourth threshold acceleration value. Collecting more than more individual acceleration data and comparing the individual measurement data with an individual threshold data can effectively determine if the capsule is accelerated in a specific pattern, according to a request to confirm turning on the capsule. By doing so, the false positive result can be effective minimized or actually eliminated. At this time period, the individual acceleration data is created by a user through a series of hand motions to purposely let the acceleration sensor detect an acceleration data greater than the predetermined third or fourth threshold acceleration value.

At the third acceleration period, while the capsule is conditioned at pre-working state, in a second example, the capsule is either continued to be monitored for acceleration data or the acceleration data is not to be collected, a wireless communication module is turned on to request confirmation from a user if the capsule is intended to be turned on. Such steps including turning on a wireless communication unit between the capsule and an external user interface; receiving a command from the external user interface to turn on the capsule.

At the third acceleration period, in a second example, the capsule is either continued to be monitored for acceleration data or the acceleration data is not to be collected, a communication module is turned on to alert a user or request confirmation from a user if the capsule is intended to be turned on. Such steps include turning on a LED inside the capsule to alert a user and/or requesting confirmation; requesting a user to input command through an external user interface or requesting a user to input a hand motion so confirm the turning on the capsule device. In one example, the LED light blinks twice to request further input from a user.

The hand motion, disclosed herein, is required to generate requested either combined or individual acceleration data in different axis, wherein the combined or individual acceleration data is significantly and measurably different from any acceleration data that can be detected while the capsule is in a non-working state.

In one example, the third and/or fourth threshold acceleration value is set to between 3-5 g, so that the value of the acceleration is measurably different created by shipping during storage or shelf time. Wherein g is the Gravitational acceleration of a 9.8 m/s$^2$ on earth.

In another example, a threshold value requires not only a certain acceleration value but also a certain acceleration direction, and the direction of acceleration is distinctive to any directions that can be created by shipping during storage or shelf time. For instance, the threshold direction requirement can be very strictly perpendicular to a ground level, indicating a hand motion of moving the capsule up and down. In another instance, the threshold direction requirement can be very strictly horizontal to a ground level, indicating a hand motion of moving the capsule left and right.

In another example, when the capsule is conditioned at the pre-working state and ready for a user confirmation if the capsule should be turned on. The confirmation protocol can include more than one hand motions in a particular sequence so that the capsule will not be turned on false positively. Even though the collected combined, individual acceleration data, or even the direction of acceleration are not very distinctive from other unexpected situations, but the sequence of individual occurrence of the acceleration data and acceleration directions can be used to accurately determine if the sensor data is from a hand motion of a user who confirms to turn on the capsule device.

In order to preserve power consumption, the third acceleration period has a preset time limit. Once the preset time limit for third acceleration period expires, the capsule is sent back to the non-working state, including monitoring acceleration of the capsule in three dimensions at a first sampling frequency for a first period and calculating a first acceleration value. The time limit or interval for the third acceleration time period is between about 5 s-1 minute. In one example the time limit or interval for the third acceleration time period is about 10 s.

Figure 2:
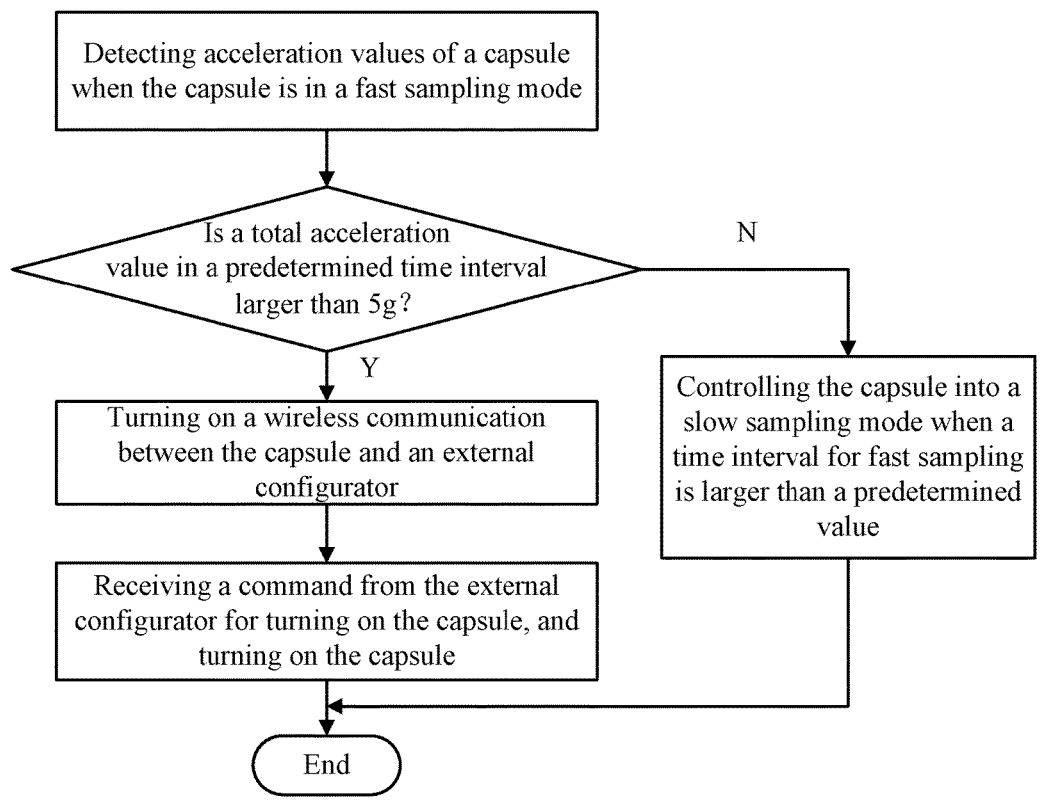
FIG. 2 diagrammatically illustrates a process flow diagram of one embodiment method in accordance with aspects of the present invention.
Figure 3:
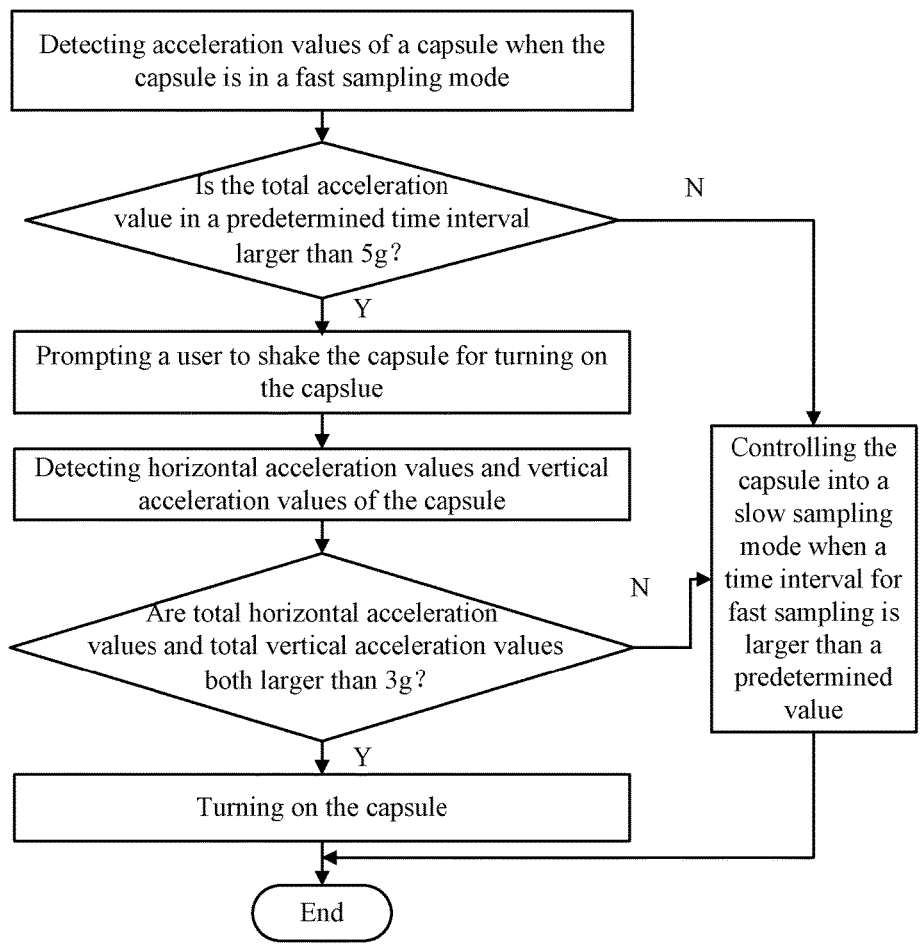
FIG. 3 diagrammatically illustrates a process flow diagram of another embodiment method in accordance with aspects of the present invention.

FIGS. 2 and 3 illustrate an actual example of the method disclosed here. In one embodiment, the method includes the following steps. Detecting a first acceleration data at a low sample mode; if the first acceleration data is more than a first threshold acceleration value, then collecting a second acceleration data at a fast sample mode; if a combined acceleration data for more than one axes is greater than a second threshold acceleration value, then placing the capsule for a pre-working state; Turning on a wireless communication unit between the capsule and an external user interface; receiving a command from the external user interface to turn on the capsule; and turning on the capsule. If the combined acceleration data is less than the second threshold value, sending the capsule back to non-working state including monitoring acceleration of the capsule in three dimensions at a low sample mode for a first period and calculating a first acceleration value.

In another embodiment, the method disclosed herein include the following steps: detecting a second group of individual acceleration data along individual acceleration axis under a fast sample mode for the second time period; determining if the total acceleration data based on the second group of individual acceleration data in the second time period exceed a second threshold acceleration value, which is 5 g, wherein g is the Gravitational acceleration of a 9.8 m/s² on earth; Requesting a user to input one or more hand motion to generate a third group acceleration data purposely; detecting the third group of horizontal acceleration data and a vertical acceleration data; if the combined acceleration data based on the third group of horizontal acceleration data and a vertical acceleration data exceed a third threshold acceleration value within the third time period, then turning on the capsule; otherwise sending the capsule back into non-working state by monitoring acceleration of the capsule in three dimensions at a first frequency for a first period and calculating a first acceleration data; and monitor the capsule at a fast sample mode when the first acceleration data exceeds a first threshold acceleration value.

The present invention is also directed to systems that implemented in the foregoing method steps. The system includes a capsule device. Optionally, the system further includes an external user interface to be used in communication with the capsule device.

The capsule device is configured to navigate through a patient's GI track. The capsule device comprises a housing, an acceleration sensor, a microcontroller unit, and a power supply. In accordance with the aspects of the present invention, the housing has a length L, which is a longest dimension of the capsule. The acceleration sensor is configured to detect an acceleration of the capsule in three dimensions at a first frequency at a first time period, wherein the acceleration sensor has three axes, x, y, and z. The z-axis of the acceleration sensor is parallel to the length L of the capsule housing, and x and y-axes of the acceleration sensor are perpendicular to the length L of the capsule housing. The microcontroller unit is connected to acceleration sensor and configured to take input from the acceleration sensor, perform calculations and determine the current state of the capsule. The current state includes a first period, a second period or a third period. The capsule device also comprises a power supply, which provides power to the acceleration sensor, microcontroller unit and capsule initiation unit. The capsule initiation unit works in the capsule pre-working state. The capsule initiation unit sends alerts to a user of the capsule to request further information.

In one aspect of the present invention, the capsule device comprises a three-dimensional sensor.

In one embodiment, the capsule initiation unit comprises a wireless communication module, which sends out information to an external user interface and receives a command from the external user interface.

In another embodiment, the capsule initiation unit comprises a LED light inside the capsule housing, which is turned on, sends out alert or notification to a user that the capsule is conditioned at pre-working state, and requests further confirmation including either an input from a user interface or a hand motion.

The capsule device disclosed herein is a vibration capsule comprises a motor.

The capsule device disclosed herein is a capsule endoscope comprising an image sensor.

The capsule device disclosed herein comprises capsule functional components and capsule structural components. In accordance with the aspects of the present invention, the capsule can have any shape and geometries. The housing of the capsule device, including but is not limited to diamond, oval, elongated, marquise, dumbbell-shaped and so on. In one example, as shown in FIG. 1, the capsule device comprise is elongated and have two half domed ends. Referring to FIG. 1, the housing for the capsule device have a front end and rear end. The capsule has a length characterized as L. The acceleration sensor is placed inside the capsule and having three axes, x, y and z. The z-axis is perpendicular to the capsule length L and x and y-axis are parallel to the capsule length L. The capsule length is measured by the length of the housing protecting the capsule. In the present invention, the housing of the capsule device has an axis along the length of the capsule device.

In accordance with the aspects of the present invention, the capsule device can be of any dimension or size as long as the capsule device can be placed inside a GI track of a patient. For example, it is preferred that a capsule device can be introduced into a patient's GI track in a non-invasive method such as swallowing. The patient herein includes both human being and an animal. Referring to FIG. 1, the capsule device has a length from its front end to its rear end. In one example, the length of the capsule device is 27.6 mm. Also referring to FIG. 1, the capsule device has two half-domed ends. The diameter for the half dome ends is the diameter of the capsule device. In one example, the diameter for the capsule device is about 11.8 mm.

In accordance with the aspects of the present invention capsule device can be of any weight as long as it does not cause significant discomfort for the patient when it moves or vibrates. The weight is distributed along and around the capsule axis. As shown in FIG. 1, the power supply unit, the acceleration sensor and other functional units are arranged along the length of the capsule device. In one example, the weight of the capsule is less than 6 g. In another example, the weight of the capsule is less than 5 g. In still another example, the weight of the capsule is less than 4.5 g. Further, the capsule device disclosed herein, is configured to generate either a stirring or motion to massage the GI track wall to improve the in vivo digestive conditions. The weight of the capsule devices is proportional related to the effectiveness of the massages. In one example, the weight of the capsule is more than 2 g. In another example, the weight of the capsule is less than 3 g. In still another example, the weight of the capsule is less than 4 g. In still another example, the weight of the capsule is more than 4.5 g.

In one embodiment, power supply unit provides power to all the capsule functional units in the capsule device through a power management unit. In one example, the power management unit comprises a microcontroller and other units to manage power usage of the capsule to achieve ultimate low power consumption.

In accordance with the aspect of the present invention, the wireless communication unit disclosed herein can be selected from a Rf communication method, AC current-magnetic field interactive method, and/or in body contact electrode method. In one embodiment, wireless communication unit includes Rf antennas, a Rf transceiver module, a build in or a separate microcontroller on PCB Through the wireless communication unit, the capsule device can establish a connection with a Bluetooth device, which in turn communicates with an external user interface for example a smart phone or Internet data center or a cloud server center. The Rf transceiver can use either 433 MHz, or 2.4 GHz as communication sampling frequency.

In another embodiment, the wireless communication unit receives information from a microcontroller unit, which compare and calculate sensor data in order to identify the current state of the capsule device.

In one embodiment, the external user interface of an external device is a smart phone user interface, which further connected to a network with a data center or cloud service center. The external device is a user specific device that can retrieve specific individual capsule identification information from the wireless communication unit. A user can customize a user specific sequence of hand motions or preferences as confirmation to turn on the capsule device.

In one aspect of the present invention, the capsule device comprises a 3 dimensional acceleration sensor, wherein the acceleration sensor has three axes in three dimensions and can detect accelerations in the three dimensions. In another aspect of the present invention, the acceleration sensor is only a one-dimensional sensor. The one-dimensional sensor has only one axis and can only detect acceleration in one dimension. When the one dimension sensor is used in capsule, the direction is indicated as the z direction, parallel to the length direction of the capsule.

In one embodiment, the method to use a capsule device comprises only one-dimension acceleration sensor, comprises confirming to turn on a capsule by collecting acceleration data along its length direction twice but in opposite directions. For example, a user of the capsule device can hold the capsule along its length direction, so that the length direction is positioned vertically and moving the capsule up and down. Then the capsule can be flipped and same hand motion is performed again. In this embodiment, when the capsule is packaged and under shipment, the capsule is lying down having its length direction horizontal rather than vertical. Then when the capsule is needed to be turned on, moving the capsule along its length direction up and down can create acceleration. Then the capsule is turned 180 degrees and the hand motion is created again. The acceleration created by the individual hand motion, and in combination with a second one following right afterwards, jointly created a capsule movement pattern that has will not be encountered during regular shipment.

In the aforementioned method of using the capsule device, the sample rate or sample frequency detected by the acceleration sensor can be stored in a history file with specific user or geographic information.

It will be appreciated by those skilled in the art that the above discussion is for demonstration purpose; and the examples discussed above are some of many possible examples. Other variations are also applicable.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to affect such feature, structure, or characteristic in connection with other ones of the embodiments. Furthermore, for ease of understanding, certain method procedures may have been delineated as separate procedures; however, these separately delineated procedures should not be construed as necessarily order dependent in their performance. That is, some procedures may be able to be performed in an alternative ordering, simultaneously, etc. In addition, exemplary diagrams illustrate various methods in accordance with embodiments of the present disclosure. Such exemplary method embodiments are described herein using and can be applied to corresponding apparatus embodiments, however, the method embodiments are not intended to be limited thereby.

Although few embodiments of the present invention have been illustrated and described, it would be appreciated by those skilled in the art that changes may be made in these embodiments without departing from the principles and spirit of the invention. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein. As used in this disclosure, the term "preferably" is non-exclusive and means "preferably, but not limited to." Terms in the claims should be given their broadest interpretation consistent with the general inventive concept as set forth in this description. For example, the terms "coupled" and "connect" (and derivations thereof) are used to connote both direct and indirect connections/couplings. As another example, "having" and "including", derivatives thereof and similar transitional terms or phrases are used synonymously with "comprising" (i.e., all are considered "open ended" terms)—only the phrases "consisting of" and "consisting essentially of" should be considered as "close ended". Claims are not intended to be interpreted under 112 sixth paragraph unless the phrase "means for" and an associated function appear in a claim and the claim fails to recite sufficient structure to perform such function.

What is claimed is:

1. A method, comprising:
changing a capsule from a non-working state to a pre-working state and subsequently turning on the capsule based on acceleration data measured by an acceleration sensor inside the capsule, comprising:
step 1: monitoring acceleration data of the capsule at a first sampling frequency for a first period and determining a first acceleration value;
step 2: monitoring acceleration data of the capsule in three dimensions at a second sampling frequency for a second period and combining the acceleration data in three dimensions to obtain a total second acceleration value, after the first acceleration value is determined to be higher than a first threshold value, wherein the second sampling frequency is higher than the first sampling frequency; and
step 3: placing the capsule in a pre-working state before turning on the capsule if the total second acceleration value is more than a second threshold value, monitoring horizontal and vertical acceleration data, and comparing with a third threshold value, for a third period;
or going back to step 1, when the third period exceeds a predetermined time interval.

2. The method of claim 1, wherein
placing the capsule in the pre-working state further comprises instructing to turn on the capsule through a wireless communication unit.

3. The method of claim 1, wherein
placing the capsule in the pre-working state further comprises requesting a user of the capsule to provide instruction to turn on the capsule by using a LED of the capsule.

4. The method of claim 1, wherein
placing the capsule in the pre-working state further comprises requesting a user to input a hand motion to purposely change an acceleration of the capsule as a confirmation to turn on the capsule.

5. The method of claim 1, wherein the third threshold value is between 3 g-5 g and g is the Gravitational acceleration of a 9.8 m/s$^2$ on earth.

6. The method of claim 1, wherein the first sampling frequency is between 0.2-8 Hz.

7. The method of claim 1, wherein the second sampling frequency is between 10-60 Hz.

8. The method of claim 1, wherein the second period is less than 3 seconds.

9. The method of claim 1, wherein the third period is between 5 s-1 minute.

10. The method of claim 1, wherein the second threshold acceleration value is 5 g and g is the Gravitational acceleration of a 9.8 m/s$^2$ on earth.

11. The method of claim 1, wherein the third threshold acceleration value further includes a direction.

12. The method of claim 1, wherein in step 3, the step of monitoring horizontal and vertical acceleration data, and comparing with a third threshold value, further comprises
monitoring horizontal and vertical acceleration data and its sequence of occurrences and comparing with a third threshold value and fourth threshold value and sequence of occurrences.

\* \* \* \* \*